US00PP14889P2

(12) United States Plant Patent
Osiecki

(10) Patent No.: US PP14,889 P2
(45) Date of Patent: Jun. 8, 2004

(54) SPATHIPHYLLUM PLANT NAMED 'RAYMOND P. OGLESBY'

(50) Latin Name: *Spathiphyllum hybrid*
Varietal Denomination: Raymond P. Oglesby

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 10/637,055

(22) Filed: Aug. 7, 2003

(51) Int. Cl.[7] ..... A01H 5/00
(52) U.S. Cl. ..... Plt./364
(58) Field of Search ..... Plt./364

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Spathiphyllum plant named 'Raymond P. Oglesby', characterized by its compact, symmetrical, bushy, upright and outwardly arching plant habit; small to medium stature; vigorous and freely clumping growth habit; glossy, thick and very dark green-colored leaves; early and freely flowering habit; large white-colored spathes that are positioned above the foliage on strong and erect peduncles; and good postproduction longevity.

1 Drawing Sheet

Botanical classification/cultivar designation: *Spathiphyllum hybrid* cultivar Raymond P. Oglesby.

BACKGROUND OF THE INVENTION

The present Invention relates to a new and distinct cultivar of Spathiphyllum plant, botanically known as *Spathiphyllum hybrid,* and hereinafter referred to by the cultivar name Raymond P. Oglesby.

The new cultivar is a product of a planned and controlled breeding program conducted by the Inventor in Altha, Fla. The objective of the breeding program is to create new compact and vigorous Spathiphyllum cultivars with dark green foliage and freely flowering habit.

The new cultivar originated from a cross-pollination made by the Inventor in July, 1994 of the Spathiphyllum hybrid cultivar S9, disclosed in U.S. Plant Pat. No. 9,901, as the female or seed parent and a proprietary Spathiphyllum hybrid seedling selection identified as code number 91-FF-1, not patented, as the male or pollen parent. The cultivar Raymond P. Oglesby was discovered and selected by the Inventor as a single plant within the progeny of the stated cross-pollination in a controlled environment in Altha, Fla. in July, 1995.

Asexual propagation of the new cultivar by tissue culture since November, 1998, in a laboratory in Altha, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature and light intensity without, however, any variance in genotype.

The following traits have been repeatedly observed and are determined to be the unique characteristics of 'Raymond P. Oglesby'. These characteristics in combination distinguish 'Raymond P. Oglesby' as a new and distinct Spathiphyllum cultivar:

1. Compact, symmetrical, bushy, upright and outwardly arching plant habit; small to medium stature, suitable for 10 to 20-cm containers.
2. Vigorous and freely clumping growth habit.
3. Glossy, thick and very dark green-colored leaves.
4. Early and freely flowering habit.
5. Large white-colored spathes that are positioned above the foliage on strong and erect peduncles.
6. Good postproduction longevity.

Plants of the new Spathiphyllum can be compared to plants of the female parent, the cultivar S9. In side-by-side comparisons conducted in Altha, Fla., plants of the new Spathiphyllum differed from plants of the cultivar S9 in the following characteristics:

1. Plants of the new Spathiphyllum were larger and more outwardly arching than plants of the cultivar S9.
2. Plants of the new Spathiphyllum had a more vigorous and freely clumping growth habit than plants of the cultivar S9.
3. Plants of the new Spathiphyllum had larger, thicker, glossier and darker-green colored leaves than plants of the cultivar S9.
4. Plants of the new Spathiphyllum were not as freely flowering as plants of the cultivar S9, but plants of the new Spathiphyllum had larger spathes and longer and thicker peduncles than plants of the cultivar S9.

Plants of the new Spathiphyllum can be compared to plants of the male parent, the selection 91-FF-1. In side-by-side comparisons conducted in Altha, Fla., plants of the new Spathiphyllum differed from plants of the selection 91-FF-1 in the following characteristics:

1. Plants of the new Spathiphyllum were smaller and more compact than plants of the selection 91-FF-1.
2. Plants of the new Spathiphyllum had a more vigorous and freely clumping growth habit than plants of the selection 91-FF-1.

3. Plants of the new Spathiphyllum had smaller leaves and shorter petioles than plants of the selection 91-FF-1.
4. Plants of the new Spathiphyllum flowered earlier and were more freely flowering than plants of the selection 91-FF-1.
5. Plants of the new Spathiphyllum had smaller spathes and shorter peduncles than plants of the selection 91-FF-1.

Plants of the new Spathiphyllum can be compared to plants of the Spathiphyllum cultivar Petite, not patented. However, in side-by-side comparisons conducted in Altha, Fla., plants of the new Spathiphyllum differed from plants of the cultivar Petite in the following characteristics:

1. Plants of the new Spathiphyllum were more larger and more outwardly arching than plants of the cultivar Petite.
2. Plants of the new Spathiphyllum had a more vigorous and freely clumping growth habit than plants of the cultivar Petite.
3. Plants of the new Spathiphyllum had larger, thicker, glossier and darker green leaves than plants of the cultivar Petite.
4. Plants of the new Spathiphyllum flowered earlier and were more freely flowering than plants of the cultivar Petite.
5. Plants of the new Spathiphyllum had larger spathes and thicker and stronger peduncles than plants of the cultivar Petite.
6. Spathes of plants of the new Spathiphyllum were positioned closer to the foliage than spathes of plants of the cultivar Petite.

Plants of the new Spathiphyllum can also be compared to plants of the Spathiphyllum cultivar S4, disclosed in U.S. Plant Pat. No. 10,013. However, in side-by-side comparisons conducted in Altha, Fla., plants of the new Spathiphyllum differed from plants of the cultivar S4 in the following characteristics:

1. Plants of the new Spathiphyllum were larger and more outwardly arching than plants of the cultivar S4.
2. Plants of the new Spathiphyllum had a more vigorous and freely clumping growth habit than plants of the cultivar S4.
3. Plants of the new Spathiphyllum had larger and thicker leaves than plants of the cultivar S4.
4. Plants of the new Spathiphyllum were not as freely flowering as plants of the cultivar S4.
5. Plants of the new Spathiphyllum had larger spathes and thicker and stronger peduncles than plants of the cultivar S4.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Spathiphyllum. The photograph comprises a side perspective view of a typical plant of 'Raymond P. Oglesby' grown in a container.

DETAILED BOTANICAL DESCRIPTION

The aforementioned photographs and following observations and measurements describe 69-week old plants (from planting rooted tissue-cultured plantlets) grown in Altha, Fla., in a polycarbonate-covered greenhouse and under commercial production conditions in 20-cm containers with one plant per container. During the production of the plants, day temperatures ranged from 24 to 32° C., night temperatures ranged from 22 to 25° C. and light levels were about 800 to 1,200 foot-candles.

In the following description, color references are made to The Royal Horticultural Society Colour Chart, 1995 Edition, except where general terms of ordinary dictionary significance are used.

Botanical classification: Spathiphyllum hybrid cultivar Raymond P. Oglesby.

Parentage:

*Female parent.*—*Spathiphyllum hybrid* cultivar S9, disclosed in U.S. Plant Pat. No. 9,901.

*Male parent.*—Proprietary *Spathiphyllum hybrid* seedling selection identified as code number 91-FF-1, not patented.

Propagation:

*Type.*—By tissue culture.

*Time to initiate roots on a tissue-cultured cutting.*—Summer: About 18 to 21 days at 25 to 30° C. soil temperature. Winter: About 24 to 28 days at 22 to 27° C. soil temperature.

*Time to produce a fully-rooted tissue-cultured plantlet.*—Summer: About 91 days at 25 to 30° C. soil temperature. Winter: About 98 days at 22 to 27° C. soil temperature.

*Root description.*—Primary roots, very thick and fleshy; lateral branch roots, fine; primary and lateral roots white in color and abundant.

Plant description:

*Plant shape.*—Compact, upright, outwardly arching and symmetrical plant habit; small to medium stature, plants of the new Spathiphyllum are typically grown in 10 to 20-cm containers.

*Growth habit.*—Erect when young, becoming outwardly arching as leaves develop. Freely clumping and bushy full appearance; about 15 clumps per plant. Vigorous growth habit and rapid growth rate.

*Plant height.*—About 54 cm from soil level to top of leaf plane and about 85 cm from soil level to spathe apices.

*Plant spread.*—About 92 cm.

*Foliage description.*—Length: About 28.5 cm. Width: About 14 cm. Shape: Ovate. Apex: Acuminate; twisting. Base: Obtuse. Margin: Entire; undulate. Aspect: Initially upright, then outwardly arching. Surface: Midrib and lateral veins sunken on upper surface and prominent on lower surface; upper surface of blade convex between veins, lower surface of blade concave between veins; upper and lower surfaces rugose. Texture, upper and lower surfaces: Leathery, thick; smooth, glabrous; durable and flexible. Luster, upper and lower surfaces: Glossy; upper surface glossier than lower surface. Venation pattern: Pinnate; about 27 pairs of primary veins per leaf. Color: Young leaves, upper surface: More green than 147A. Young leaves, lower surface: Close to 147B. Fully expanded leaves, upper surface: Much darker than 147A. Fully expanded leaves, lower surface: Close to 147B. Midvein and lateral veins, upper surface: Much darker green than 147A. Midvein and lateral veins, lower surface: More green than 147A.

Petiole: Length: About 36 cm. Diameter, just below the geniculum: About 7 mm. Petiole sheath, length: About 23.5 cm. Petiole sheath, width at midpoint, unfurled: About 9 mm. Petiole sheath, apex: Rounded. Geniculum length: About 5.1 mm. Geniculum diameter: About 7.5 mm. Geniculum aspect: Straight to slightly curved. Color: Petiole: Close to 147A. Petiole sheath: Close to 147A. Geniculum: More green than 147A.

Inflorescence description:

*Inflorescence arrangement/quantity.*—Concave spathes with spadices held above the foliage on strong and erect peduncles. Freely flowering; typically at least four or five developing and open spathes per plant at one time; inflorescences arise from the petiole sheath.

*Time to flower.*—Plants start flowering about 30 weeks after planting rooted tissue-cultured plantlets.

*Inflorescence longevity.*—Spathes generally maintain white color for about 4 to 4.5 weeks on the plant becoming eventually entirely green with subsequent development. As cut flowers, spathes maintain good substance for about one to two weeks.

*Fragrance.*—None detected.

*Inflorescence buds.*—Length: About 9 cm. Diameter, widest point: About 1 cm. Shape: Columnar. Color: Close to 155A.

*Spathe.*—Length: About 15.5 cm. Width: About 9.7 cm. Depth: About 3.5 cm. Shape: Ovate. Apex: Acuminate, elongated; twisted. Base: Obtuse to oblique. Aspect: Concave. Color: Front and back surfaces: Close to 155D; midrib, back surface, more green than 147A. Front and back surfaces with subsequent development: More green than 144A; midrib, back surface, more green than 147A.

*Spadix.*—Length: About 8.3 cm. Diameter: About 1.8 cm. Color: Close to 158A gradually becoming more green than 147A with subsequent development. Quantity of flowers per spadix: More than 100. Stamens: Anthers and filaments minute. Pollen: None observed. Pistils: Conical; pistillate flowers extend about 4.5 mm beyond the staminate flowers; close to 158A in color.

*Peduncle.*—Length: About 63 cm. Diameter, at midpoint: About 5 mm. Aspect: Straight, erect. Color: More green than 146A.

*Fruit/seed.*—Fruit and seed production have not been observed.

Disease/pest resistance: Plants of the new Spathiphyllum have not been observed to be resistant to pathogens or pests common to Spathiphyllum.

It is claimed:

1. A new and distinct cultivar of Spathiphyllum plant named 'Raymond P. Oglesby', as illustrated and described.

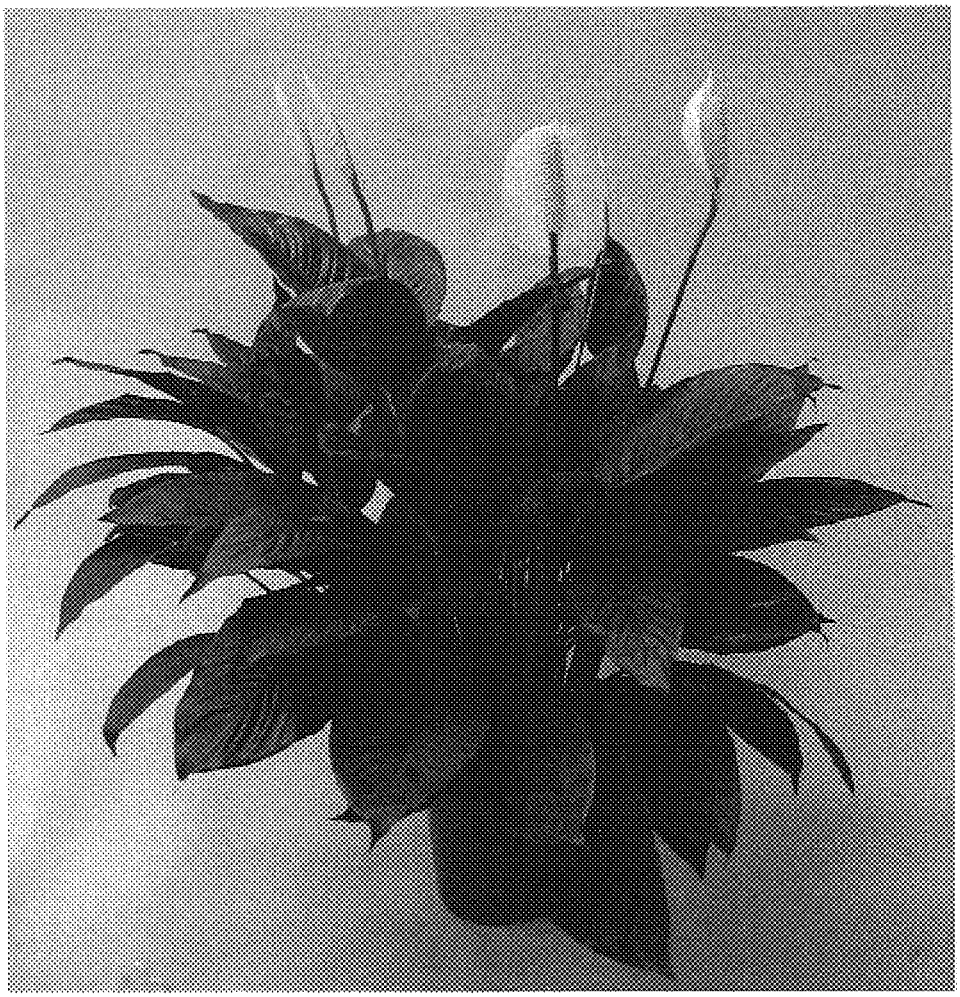

* * * * *